United States Patent [19]

Battey et al.

[11] Patent Number: 4,488,985
[45] Date of Patent: Dec. 18, 1984

[54] PHOSPHORAMIDATES CONTAINING A P-PHENYLENEDIAMINE GROUP

[75] Inventors: Paul K. Battey, Harrogate; Peter Hope, Hollingworth Lake, both of England

[73] Assignee: Akzona Incorporated, Enka, N.C.

[21] Appl. No.: 516,143

[22] Filed: Jul. 21, 1983

Related U.S. Application Data

[62] Division of Ser. No. 399,580, Jul. 19, 1982, Pat. No. 4,418,022.

[30] Foreign Application Priority Data

Jul. 20, 1981 [NL] Netherlands .................. 8103418

[51] Int. Cl.³ .................. C09K 15/32; C08K 5/49
[52] U.S. Cl. .................. 252/400 A; 252/406; 524/81; 524/136; 524/148; 524/151; 106/243; 106/270
[58] Field of Search .................. 252/400.21, 406; 524/81, 136, 147, 148, 151; 106/243, 270

[56] References Cited

U.S. PATENT DOCUMENTS 3,914,344 10/1975 Schwarzenbach et al. ........ 524/136
4,006,117 2/1977 Merrifield et al. .................. 524/151
4,383,066 5/1983 Sugio .................. 524/147

Primary Examiner—Maurice J. Welsh
Assistant Examiner—Garnette D. Draper
Attorney, Agent, or Firm—Francis W. Young; Jack H. Hall

[57] ABSTRACT

Novel phosphoramidates of the general formula:

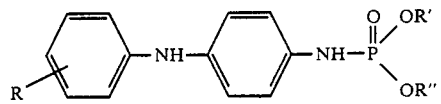

wherein R, R' and R" represent certain specified substituent groups, are useful as stabilizing agents for organic materials, such as natural and synthetic rubbers and lubricating oils. The combined use of these compounds with certain sulfur-containing compounds shows a surprising synergistic effect.

33 Claims, No Drawings

PHOSPHORAMIDATES CONTAINING A P-PHENYLENEDIAMINE GROUP

This is a division of application Ser. No. 399,580, filed July 19, 1982 now U.S. Pat. No. 4,418,022.

BACKGROUND OF THE INVENTION

The present invention relates to novel phosphoramidate compounds containing a p-phenylenediamine group, to compositions containing these compounds for stabilizing organic materials, and to lubricating oils or shaped articles of organic materials containing a stabilizing amount of the composition.

It is well known in the art that many N-substituted paraphenylenediamines posses the serious drawbacks of changing the visual appearance of organic materials which are to be stabilized.

SUMMARY OF THE INVENTION

The present invention provides novel compounds of the general formula:

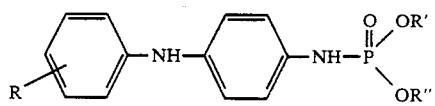

wherein R is a hydrogen atom, a straight-chain or branched-chain alkyl or alkoxy group, or cycloalkyl or cycloalkoxy group containing from 5 to 8 carbon atoms, and wherein R' and R" may be the same or different and each represents a substituted or unsubstituted straight-chain or branched-chain alkyl group having 1 to 22 carbon atoms, a substituted or unsubstituted cycloalkyl group having 5 to 8 carbon atoms, an alkenyl group having 3 to 22 carbon atoms, a substituted or unsubstituted phenyl group, an alkylphenyl group containing from 7 to 14 carbon atoms, or an aralkyl group containing from 7 to 15 carbon atoms, or alternatively wherein R' and R" together are a 1,2- or 1,3-alkylene group containing from 2 to 8 carbon atoms or an o-arylene group containing from 6 to 10 carbon atoms.

The novel compounds of the present invention are particularly useful as antioxidants when incorporated into natural and synthetic rubbers where, unlike conventional p-phenylenediamine antioxidants, they have been found to be non-staining and in certain instances non-pigmenting. Preferred compounds are those in which R is a hydrogen atom and R' and R" are the same or different and each represents an alkyl group containing 1 to 18 carbon atoms, an alkylphenyl group containing 7 to 14 carbon atoms or an aralkyl group containing 7 to 15 carbon atoms, or alternatively wherein R' and R" together are ethylene or o-phenylene. Particularly preferred compounds are those in which R is a hydrogen atom and R' and R" are the same or different and at least one of them represents an ethyl, n-butyl, lauryl or phenyl group. A preferred compound of the invention is a compound of the formula:

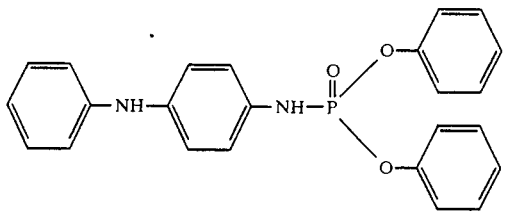

The compounds of the present invention are advantageously used in the stabilization of organic materials, such as waxes and synthetic resins, as well as synthetic rubbers of which styrenebutadiene rubber (SBR) and nitrile rubber are exemplary, and especially natural rubber and lubricating oils. In contrast with most known p-phenylenediamine-type antioxidants the present compounds, although derived from the staining antioxidants, are non-staining or stain so slightly as to produce negligible discoloration in the stabilized product, while maintaining a high degree of antioxidant activity.

The antioxidants of the present invention may be employed to produce dispersions or emulsions which are mixed with a rubber latex during coagulation and which protect this latex during subsequent treatment. They need not be added to the rubber at the latex stage, but may instead be used as antioxidants when added to rubber crumb or baled crumbs at the mill or during other fabrication stages. Thus, the compounds of the present invention may be incorporated into an oxidizable organic material, such as natural rubber, in an amount from about 0.005 to 5 parts per 100 parts of material, to afford non-staining compositions having an improved stability towards oxidation by atmospheric oxygen. The compounds of the present invention are also particularly useful for the stabilization of lubricants and either synthetic or petroleum based greases and oils, such as for example aliphatic esters, polyalkylene oxides, silicones, phosphoric acid esters, silicic acid esters and polyfluorinated hydrocarbons. Lubricant oils of petroleum origin into which the antioxidants of the present invention may be incorporated include the motor oils, transmission oils, cutting oils, and hydraulic oils known in the industry. The compounds of the invention may be incorporated into synthetic greases such as alkali metal, alkaline earth metal and aluminum based greases in solid or semi-solid form. Furthermore, the compounds of the present invention may be added to motor fuels that contain saturated and/or unsaturated blends of hydrocarbon materials. The combined use of the products of the invention and certain sulfur-containing compounds is found to have a tremendous synergistic effect in the inhibition of oxidation in lubricating oils.

Sulfur-containing compounds which have a synergistic effect with the compounds of the present invention include sulfur compounds having other uses in lubricating oil formulations. Examples of these sulfur compounds are the disulfides, including di-n-butyl disulfide, dicyclohexyl disulfide, 2,2'-(dicarboethoxy)diethyl disulfide and dibenzyl disulfide. Other suitable sulfur compounds are sulfurized triisobutylene and benzothiadiazole, and the sulfurized Diels-Alder adducts disclosed in U.S. Pat. No. 3,498,915. Good results are obtained with dibenzyldisulfide, zinc dialkyldithiophosphates, zinc diaryldithiophosphates, sulfurized sperm oil or phosphosulfurized-pinene. A synergistic effect is generally obtained if, per 10 parts by weight of the sulfur compound, the composition contains from 6 to 14 parts by weight of the antidegradant of the present invention. The minimum amount in which either stabilizer must be present in order to give the desired results is generally in the range of from 0.005 to 5% by weight, the amount in which each component is added usually being in the range of 0.2 to 5% by weight.

The compounds of the present invention are manufactured by reacting equimolar amounts of a p-aminodiphenylamine with a halophosphate ester, preferably a chlorophosphate ester. Advantageously, at least an equimolar amount of a tertiary amine such as triethylamine, triisopropylamine or pyridine may be added to neutralize the hydrogen halide acid produced. Examples of suitable solvents in which the reaction may be carried out are: dimethylacetamide, dimethylformamide, tetrahydrofuran, diethyl ether, or dioxane; esters such as ethyl acetate; aromatic hydrocarbons such as benzene or toluene; aliphatic hydrocarbons and mixtures such as hexane, heptane, or ligroin. The starting products are known or can be readily manufactured in accordance with generally known methods.

The manufacture and use of the compounds according to the invention are described in more detail in the following Examples, in which "parts" denotes parts by weight and "%" denotes percentages by weight.

Example I

Diphenylchlorophosphate (127 g.) was dissolved in 50 cm$^3$ dry toluene to form a solution which was added over a period of 1 hour to a stirred mixture of 82.8 g. 4-aminodiphenylamine, 450 cm$^3$ dry toluene and 50 g. triethylamine. The reaction was mildly exothermic, the temperature of the reaction mixture rising from 20° C. to 33° C. while adding the solution. Stirring was continued for a further 18 hours, after which period a thick paste was obtained. The solid was filtered off and partitioned by extraction with chloroform and water. The toluene filtrate was evaporated to dryness under vacuum, and the residue was similarly partitioned between chloroform and water. The two chloroform solutions were combined, dried over anhydrous Na$_2$SO$_4$, and evaporated down to afford a light grey solid in a yield of 94% (175.6 g.) and having a melting point of 126.5°–128° C.

This product can be recrystallized from methanol to give a white crystalline solid having a melting point of 127.5°–128° C. and at a yield of 85% (158.7 g.). Other phosphoramidates can be prepared in an analogous manner.

EXAMPLE II

Stabilization of Natural Rubber

The product of Example I (Compound A) was evaluated as an antioxidant in a comparison with Compound B, 2,2'-methylene-bis-(4-methyl-6-tertiarybutyl) phenol, in the following standard rubber formulations:

|  | parts by weight |
|---|---|
| Natural Rubber (SMR 5) | 100 |
| carbon black | 45 |
| zinc oxide | 5 |
| stearic acid | 3 |
| N—cyclohexyl-2-benzothiazyl sulphenamide | 0.5 |
| sulfur | 2.5 |
| antioxidant | 0.25–1 |

Vulcanization was carried out at 142° C. for 35 minutes. The following physical properties of test samples were measured in accordance with DIN 53504:

| tensile strength (T) | N/cm$^2$ |
|---|---|
| elongation at break (E) | % |
| modulus (M) | N/cm$^2$ |

After the samples had been subjected to hot air aging at 70° C. for 7 days and to oxygen aging by the method of Bierer and Davis (DIN 53508) for 2 days at 70° C. and at a pressure of 21 atmospheres, the above properties were measured again. The effect on the physical properties of the test samples expressed as a percentage of the initial measured values is shown in Table I. For the long term oxygen aging evaluation the same conditions were used, with the exception that longer test periods were employed. The results expressed as a percentage of the initial measured values are shown in Table II (natural rubber), Table III (carbon black-filled natural rubber after hot air aging at 100° C.) and Table IV (in whiting-filled natural rubber after hot air aging at 100° C.).

The results set forth in these tables clearly show the superior stabilizing properties of the compounds of the present invention, as compared with those of a typical and widely used commercial non-staining antioxidant, 2,2'-methylene-bis-(4methyl-6-tertiarybutyl) phenol (Compound B).

TABLE I

| | | RETENTION OF PHYSICAL PROPERTIES AFTER AGING | | | | | |
|---|---|---|---|---|---|---|---|
| | | initial data in N/cm × 10 | | | percentage retention of physical properties after hot air aging | | |
| ANTIOXIDANT | Concentration in % by weight | TENSILE STRENGTH | ELONGATION AT BREAK | MODULUS | TENSILE (T) | ELONGATION (E) | MODULUS (M) |
| Compound A | 0.25 | 285 | 386 | 200 | 99 | 106 | 106 |
| | 0.5 | 307 | 464 | 190 | 88 | 90 | 114 |
| | 0.75 | 310 | 469 | 197 | 96 | 90 | 117 |
| | 1.0 | 321 | 473 | 205 | 96 | 88 | 106 |
| Compound B | 0.25 | 315 | 420 | 232 | 86 | 91 | 93 |
| | 0.5 | 321 | 548 | 184 | 88 | 73 | 120 |
| | 0.75 | 305 | 532 | 150 | 101 | 82 | 141 |
| | 1.0 | 321 | 647 | 153 | 92 | 62 | 143 |
| without antioxidant | — | 280 | 397 | 192 | 98 | 94 | 111 |

| | Concentration | percentage retention of physical properties after oxygen aging |
|---|---|---|

TABLE I-continued
RETENTION OF PHYSICAL PROPERTIES AFTER AGING

| ANTIOXIDANT | tion in % by weight | TENSILE (T) | ELONGATION (E) | MODULUS (M) |
|---|---|---|---|---|
| Compound A | 0.25 | 86 | 164 | 58 |
|  | 0.5 | 83 | 87 | 91 |
|  | 0.75 | 89 | 91 | 102 |
|  | 1.0 | 85 | 87 | 92 |
| Compound B | 0.25 | 29 | 56 | 51 |
|  | 0.5 | 48 | 67 | 69 |
|  | 0.75 | 64 | 77 | 101 |
|  | 1.0 | 69 | 70 | 99 |
| without antioxidant | — | 15 | 8 | 205 |

TABLE II
RETENTION OF PHYSICAL PROPERTIES AFTER LONG TERM OXYGEN AGING

| | | PERCENTAGE RETENTION OF PHYSICAL PROPERTIES AFTER OXYGEN AGING FOR | | | | | | | | |
|---|---|---|---|---|---|---|---|---|---|---|
| | CONCENTRATION | 5 days | | | 10 days | | | 15 days | | |
| ANTIOXIDANT | % BY WEIGHT | T | E | M | T | E | M | T | E | M |
| A | 0.25 | 69.0 | 70.4 | 74.3 | 29.3 | 61.1 | 40.0 | 17.4 | 31.6 | 0 |
|  | 0.5 | 73.8 | 83.6 | 91.9 | 52.4 | 82.9 | 70.2 | 33.6 | 80.0 | 37.8 |
|  | 0.75 | 75.9 | 88.5 | 92.5 | 57.7 | 82.4 | 75.0 | 46.3 | 83.3 | 39.0 |
|  | 1.0 | 80.1 | 87.7 | 47.8 | 62.5 | 66.1 | 30.4 | 48.7 | 87.8 | 53.5 |
| B | 0.25 | 4.4 | 9.8 | 0 | 0 | 0 | 0 | 0 | 0 | 0 |
|  | 0.5 | 6.9 | 11.5 | 13.2 | 0 | 0 | 0 | 0 | 0 | 0 |
|  | 0.75 | 22.3 | 28.2 | 18.9 | 0 | 0 | 0 | 0 | 0 | 0 |
|  | 1.0 | 23.7 | 27.8 | 18.9 | 0 | 0 | 0 | 0 | 0 | 0 |
| Without Antioxidant | — | 0 | 0 | 0 | 0 | 0 | 0 | 0 | 0 | 0 |

TABLE III

| | | PERCENTAGE RETENTION OF PHYSICAL PROPERTIES AFTER HOT AIR AGING AT 100° C. FOR | | | | | | | | | | | |
|---|---|---|---|---|---|---|---|---|---|---|---|---|---|
| | CONCENTRATION | 1 day | | | 3 days | | | 5 days | | | 7 days | | |
| ANTIOXIDANT | % BY WEIGHT | T | E | M | T | E | M | T | E | M | T | E | M |
| Compound A | 1.0 | 82 | 80 | 107 | 38 | 50 | 105 | 28 | 40 | 105 | 24 | 29 | 154 |
|  | 0.5 | 75 | 77 | 113 | 33 | 49 | 95 | 22 | 38 | 96 | 19 | 24 | 147 |
|  | 0.3 | 76 | 81 | 106 | 30 | 52 | 92 | 18 | 30 | 110 | 19 | 24 | 184 |
| Compound B | 2.0 | 73 | 77 | 112 | 33 | 45 | 139 | 23 | 30 | 140 | 28 | 25 | 212 |
|  | 1.0 | 65 | 68 | 114 | 31 | 47 | 88 | 21 | 29 | 118 | 20 | 22 | 176 |
|  | 0.5 | 71 | 71 | 113 | 33 | 49 | 87 | 23 | 34 | 105 | 22 | 26 | 147 |

(100° C. hot air aging of antioxidants in carbon black-filled natural rubber)

TABLE IV

| | | PERCENTAGE RETENTION OF PHYSICAL PROPERTIES AFTER HOT AIR AGING AT 100° C. FOR | | | | | | | | | | | |
|---|---|---|---|---|---|---|---|---|---|---|---|---|---|
| | CONCENTRATION | 1 day | | | 3 days | | | 5 days | | | 7 days | | |
| ANTIOXIDANT | % BY WEIGHT | T | E | M | T | E | M | T | E | M | T | E | M |
| Without Antioxidant | | 55 | 87 | 95 | 17 | 61 | 81 | 8 | 47 | — | 8 | 25 | — |
| Compound A | 1.0 | 88 | 93 | 107 | 72 | 84 | 124 | 65 | 79 | 125 | 32 | 62 | 136 |
|  | 0.5 | 87 | 92 | 108 | 56 | 79 | 121 | 49 | 74 | 123 | 19 | 51 | 131 |
|  | 0.3 | 88 | 93 | 105 | 55 | 77 | 120 | 31 | 64 | 124 | 23 | 55 | 125 |
| Compound B | 2.0 | 84 | 87 | 120 | 55 | 75 | 134 | 39 | 68 | 138 | 18 | 49 | 143 |

(100° C. hot air aging of antioxidants in whiting-filled natural rubber)

Example III

In this Example a comparison is made between N-isopropyl-N'-phenyl-p-phenylenediamine (compound C), an antidegradant widely used by the rubber industry and known to cause severe migration staining, and the following phophoramidates according to the invention:

N-(p-phenylaminophenyl)diethyl phosphoramidate (compound D);

N-(p-phenylaminophenyl)diphenyl phosphoramidate (compound A);

N-(p-phenylaminophenyl)dilauryl phosphoramidate (compound E); and

N-(p-phenylaminophenyl)di-n-butyl phosphoramidate (compound F).

The above compounds were characterized by IR and NMR; the following melting points were measured:

| | |
|---|---|
| Compound D | 111°–112° C.; |
| Compound E | waxy solid; |
| Compound F | 45° C. |

The above compounds were evaluated in carbon black-loaded natural rubber. The heat resistance and oxygen resistance in accordance with DIN 53508 were measured and the results compared with those obtained with compound C.

The staining test was also performed with the above compounds, and the results compared with those obtained using compound C and expressed as a percentage of the activity of the blank. In the staining test the extent to which a stabilizer tends to migrate from the rubber vulcanizate and cause discoloration upon its contact with light colored objects is measured. The rubber samples to be tested to that end contained either no stabilizer or one of the compounds C, D, A, E and F. The rubber samples were contacted with white rubber for 7 days.

The results are given in the following Table V and expressed as a percentage of the activity of the blank:

TABLE V

STAINING, HEAT RESISTANCE AND OXYGEN RESISTANCE OF ANTIOXIDANTS
IN CARBON BLACK-LOADED NATURAL RUBBER

| ANTIOXIDANT | CONCENTRATION % BY WEIGHT | HEAT RESISTANCE AS COMPARED WITH COMPOUND C | | | OXYGEN RESISTANCE AS COMPARED WITH COMPOUND C | | | % STAINING RELATIVE TO BLANK (100% = NON-STAINING) |
|---|---|---|---|---|---|---|---|---|
| | | T | E | M | T | E | M | |
| COMPOUND C (comparison) | 1 | 100 | 100 | 100 | 100 | 100 | 100 | 32 |
| COMPOUND D | 1 | 98 | 97 | 106 | 97 | 107 | 103 | 99 |
| | 2 | 101 | 94 | 83 | 106 | 105 | 104 | 100 |
| COMPOUND A | 1 | 99 | 99 | 101 | 103 | 103 | 93 | 100 |
| | 2 | 91 | 91 | 99 | 94 | 98 | 93 | 99 |
| COMPOUND E | 1 | 99 | 100 | 99 | 99 | 109 | 88 | 98 |
| | 2 | 91 | 93 | 97 | 93 | 100 | 89 | 98 |
| COMPOUND F | 1 | 95 | 93 | 103 | 102 | 100 | 102 | 96 |
| | 2 | 96 | 94 | 104 | 93 | 95 | 94 | 89 |

EXAMPLE IV

Stabilization of Mineral Oil 0.25 g. of the product of Example I (compound A) was dissolved in 49.75 g. of a mineral oil (solvent-refined paraffin base oil Risella 33, a product of the Royal Dutch/Shell Group). The solution was heated to 175° C. and air passed through it at a rate of 5 liters/hour in an open system. The induction time to oxidation was measured by oxygen analysis of the effluent gas flow. N-isopropyl-N-phenyl-p-phenylene-diamine (compound C) was used as a standard and the results are given in Table VI.

TABLE VI

| Mineral oil + antioxidant | induction time (mins.) |
|---|---|
| without antioxidant | 10 |
| 0.5% by weight of compound A | 660 |
| 0.5% by weight of compound C | 510 |
| 0.5% by weight of compound D | 600 |
| 0.5% by weight of compound E | 1260 |

EXAMPLE V

This example demonstrates the stabilization of mineral oil in the presence of a synergistic amount of a sulfur compound and a phosphoramidate according to the invention. The procedure described in Example IV was repeated using 0.5% (w/w) dibenzyldisulfide (compound P) as additive, and mixtures of compounds (A) and (P), totaling 0.5% by weight. The results are given in Table VII.

TABLE VII

| Compound A (% w/w) | Compound P (% w/w) | Induction time (hours) |
|---|---|---|
| 0.5 | 0 | 11.0 |
| 0.4 | 0.1 | 50.0 |
| 0.3 | 0.2 | 67.0 |
| 0.25 | 0.25 | 73.0 |
| 0.2 | 0.3 | 55.0 |
| 0.1 | 0.4 | 46.5 |
| 0 | 0.5 | 2.0 |

What is claimed is:

1. A composition for stabilizing an organic material such as waxes, natural and synthetic rubbers, synthetic resins, and lubricating oils, comprising:

(a) a phosphoramidate compound of the general formula:

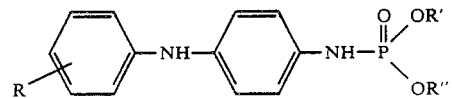

wherein R is a hydrogen atom, a straight-chain or branched-chain alkyl or alkoxy group, or cycloalkyl or cycloalkoxy group containing from 5 to 8 carbon atoms, and wherein R' and R" may be the same or different and each represents a substituted or unsubstituted straight-chain or branched-chain alkyl group having 1 to 22 carbon atoms, a substituted or unsubstituted cycloalkyl group having 5 to 8 carbon atoms, an alkenyl group having 3 to 22 carbon atoms, a substituted or unsubstituted phenyl group, an alkylphenyl group containing from 7 to 14 carbon atoms, or an aralkyl group containing from 7 to 15 carbon atoms, or alternatively wherein R' and R" together are a 1,2- or 1,3-alkylene group containing from 2 to 8 carbon atoms or an o-arylene group containing from 6 to 10 carbon atoms; and (b) a synergistic amount of a sulfur compound.

2. A composition for stabilizing an organic material, comprising:

(a) the phosphoramidate compound as set forth in claim 1, wherein R is a hydrogen atoms and R' and R" are the same or different and each represent an alkyl group containing 1 to 18 carbon atoms, an alkylphenyl group containing 7 to 14 carbon atoms or an aralkyl group containing 7 to 15 carbon atoms, or alternatively wherein R' and R" together are ethylene or o-phenylene; and (b) a synergistic amount of a sulfur compound.

3. A composition for stabilizing an organic material, comprising:
(a) the phosphoramidate compound as set forth in claim 1, wherein R is a hydrogen atom and R' and R" are the same or different and at least one of them is selected from the group including the ethyl, n-butyl, lauryl or phenyl group; and
(b) a synergistic amount of a sulfur compound.

4. A composition as claimed in claim 1, which comprises from 6 to 14 parts by weight of said sulfur compound per 10 parts by weight of said phosphoramidate compound.

5. A composition as claimed in claim 2, which comprises from 6 to 14 parts by weight of said sulfur compound per 10 parts by weight of said phosphoramidate compound.

6. A composition as claimed in claim 3, which comprises from 6 to 14 parts by weight of said sulfur compound per 10 parts by weight of said phosphoramidate compound.

7. A composition as set forth in claim 1, wherein the sulfur compound is selected from the group including di-n-butyl disulfide, dicyclohexyl disulfide, 2,2'-(dicarboethoxy)diethyl disulfide, or dibenzyl disulfide.

8. A composition as set forth in claim 1, wherein the sulfur compound is selected from the group including di-n-butyl disulfide, dicyclohexyl disulfide, 2,2'-(dicarboethoxy)diethyl disulfide, or dibenzyl disulfide.

9. A composition as set forth in claim 3, wherein the sulfur compound is selected from the group including di-n-butyl disulfide, dicyclohexyl disulfide, 2,2'-(dicarboethoxy)diethyl disulfide, or dibenzyl disulfide.

10. A composition as set forth in claim 4, wherein the sulfur compound is selected from the group including di-n-butyl disulfide, dicyclohexyl disulfide, 2,2'-(dicarboethoxy)diethyl disulfide, or dibenzyl disulfide.

11. A composition as set forth in claim 5, wherein the sulfur compound is selected from the group including di-n-butyl disulfide, dicyclohexyl disulfide, 2,2'-(dicarboethoxy)diethyl disulfide, or dibenzyl disulfide.

12. A composition as set forth in claim 6, wherein the sulfur compound is selected from the group including di-n-butyl disulfide, dicyclohexyl disulfide, 2,2'-(dicarboethoxy)diethyl disulfide, or dibenzyl disulfide.

13. A composition as set forth in claim 1, wherein the sulfur compound is selected from the group including zinc dialkyldithiophosphates, zinc diaryldithiophosphates, sulfurised sperm oil or phosphosulfurised-pinene.

14. A composition as set forth in claim 2, wherein the sulfur compound is selected from the group including zinc dialkyldithiophosphates, zinc diaryldithiophosphates, sulfurised sperm oil or phosphosulfurised-pinene.

15. A composition as set forth in claim 3, wherein the sulfur compound is selected from the group including zinc dialkyldithiophosphates, zinc diaryldithiophosphates, sulfurised sperm oil or phosphosulfurised-pinene.

16. A composition as set forth in claim 4, wherein the sulfur compound is selected from the group including zinc dialkyldithiophosphates, zinc diaryldithiophosphates, sulfurised sperm oil or phosphosulfurised-pinene.

17. A composition as set forth in claim 5, wherein the sulfur compound is selected from the group including zinc dialkyldithiophosphates, zinc diaryldithiophosphates, sulfurised sperm oil or phosphosulfurised-pinene.

18. A composition as set forth in claim 6, wherein the sulfur compound is selected from the group including zinc dialkyldithiophosphates, zinc diaryldithiophosphates, sulfurised sperm oil or phosphosulfurised-pinene.

19. An organic material such as waxes, natural and synthetic rubbers, synthetic resins, and lubricating oils subject to oxidative degradation and containing a phosphoramidate compound of the general formula:

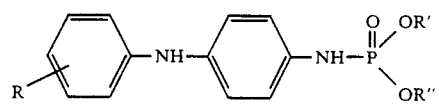

wherein R is a hydrogen atom, a straight-chain or branched-chain alkyl or alkoxy group, or cycloalkyl or cycloalkoxy group containing from 5 to 8 carbon atoms, and wherein R' and R" may be the same or different and each represents a substituted or unsubstituted straight-chain or branched-chain alkyl group having 1 to 22 carbon atoms, a substituted or unsubstituted cycloalkyl group having 5 to 8 carbon atoms, an alkenyl group having 3 to 22 carbon atoms, a substituted or unsubstituted phenyl group, an alkylphenyl group containing from 7 to 14 carbon atoms, or an aralkyl group containing from 7 to 15 carbon atoms, or alternatively wherein R' and R" together are a 1,2- or 1,3-alkylene group containing from 2 to 8 carbon atoms or an o-arylene group containing from 6 to 10 carbon atoms.

20. The organic material as set forth in claim 19, wherein R is a hydrogen atom and R' and R" are the same or different and each represent an alkyl group containing 1 to 18 carbon atoms, an alkylphenyl group containing 7 to 14 carbon atoms or an aralkyl group containing 7 to 15 carbon atoms, or alternatively wherein R' and R" together are ethylene or o-phenylene.

21. The organic material as set forth in claim 19, wherein R is a hydrogen atom and R' and R" are the same or different and at least one of them is selected from the group including the ethyl, n-butyl, lauryl or phenyl group.

22. An organic material subject to oxidative degradation and containing a stabilizer composition as set forth in claim 1.

23. An organic material subject to oxidative degradation and containing a stabilizer composition as set forth in claim 2.

24. An organic material subject to oxidative degradation and containing a stabilizer composition as set forth in claim 3.

25. An organic material subject to oxidative degradation and containing a stabilizer composition as set forth in claim 4.

26. An organic material subject to oxidative degradation and containing a stabilizer composition as set forth in claim 5.

27. An organic material subject to oxidative degradation and containing a stabilizer composition as set forth in claim 6.

28. An organic material such as waxes, natural and synthetic rubbers, synthetic resins, and lubricating oils subject to oxidative degradation and containing 0.005 to 5 parts by weight of at least one phosphoramidate compound per 100 parts by weight of said organic material, said phosphoramidate compound being of the general formula:

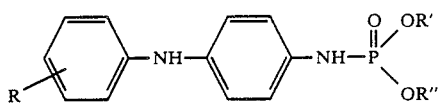

wherein R is a hydrogen atom, a straight-chain or branched-chain alkyl or alkoxy group, or cycloalkyl or cycloalkoxy group containing from 5 to 8 carbon atoms, and wherein R' and R" may be the same or different and each represents a substituted or unsubstituted straight-chain or branched-chain alkyl group having 1 to 22 carbon atoms, a substituted or unsubstituted cycloalkyl group having 5 to 8 carbon atoms, an alkenyl group having 3 to 22 carbon atoms, a substituted or unsubstituted phenyl group, an alkylphenyl group containing from 7 to 14 carbon atoms, or an aralkyl group containing from 7 to 15 carbon atoms, or alternatively wherein R' and R" together are a 1,2- or 1,3-alkylene group containing from 2 to 8 carbon atoms or an o-arylene group containing from 6 to 10 carbon atoms.

29. The organic material set forth in claim 28, wherein in said phosphoramidate compound, R is a hydrogen atom and R' and R" are the same or different and each represent an alkyl group containing 1 to 18 carbon atoms, an alkylphenyl group containing 7 to 14 carbon atoms or an aralkyl group containing 7 to 15 carbon atoms, or alternatively wherein R' and R" together are ethylene or o-phenylene.

30. The organic material set forth in claim 28, wherein in said phosphoramidate compound, R is a hydrogen atom and R' and R" are the same or different and at least one of them is selected from the group including the ethyl, n-butyl, lauryl or phenyl group.

31. The organic material set forth in claim 28, further containing a synergistic amount of a sulfur compound per 100 parts by weight of said organic material.

32. The organic material set forth in claim 29, further containing a synergistic amount of a sulfur compound per 100 parts by weight of said organic material.

33. The organic material set forth in claim 30, further containing a synergistic amount of a sulfur compound per 100 parts by weight of said organic material.

* * * * *